United States Patent [19]
Buechner et al.

[11] Patent Number: 5,268,448
[45] Date of Patent: Dec. 7, 1993

[54] CONDUCTING POLYMERS DERIVED FROM FLUORINATED THIOPHENES

[75] Inventors: Werner Buechner, Savigny; Marc Lemaire, Nanterre; Jean Roncali, Les Lilas; Robert Garreau, Sarcelles; Francis Garnier, Champigny, all of France; Etienne Hannecart, Tervuren, Belgium

[73] Assignee: Solvay S.A., Brussels, Belgium

[21] Appl. No.: 899,130

[22] Filed: Jun. 16, 1992

Related U.S. Application Data

[63] Continuation of Ser. No. 547,071, Jul. 3, 1990, abandoned.

[30] Foreign Application Priority Data

Jul. 10, 1989 [FR] France .............................. 89 09368

[51] Int. Cl.$^5$ ............................................. C08G 75/00
[52] U.S. Cl. ................................... 528/380; 252/500; 252/501.1; 528/377; 549/83
[58] Field of Search ................. 526/256; 528/377, 380

[56] References Cited

U.S. PATENT DOCUMENTS 3,052,691  9/1962  Krespan .
3,197,480  7/1965  England .
4,711,742  12/1987  Jen ...................................... 524/609

FOREIGN PATENT DOCUMENTS 0203438  12/1986  European Pat. Off. .
2624126  6/1989  France .

OTHER PUBLICATIONS

William J. Middleton, "New Fluorinating Reagents, Dialkylaminosulfur Fluorides", *Journal of Organic Chemistry*, vol. 40, pp. 574 to 578 (1975).

*Primary Examiner*—Christopher Henderson
*Attorney, Agent, or Firm*—Spencer, Frank & Schneider

[57] ABSTRACT

Substituted thiophenes of general formula:

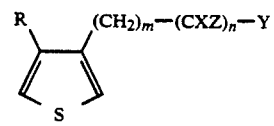

in which:

R represents hydrogen atom or an aliphatic group containing from 1 to 4 carbon atoms, X and Z may be identical or different and represent a hydrogen atom or a fluorine atom, Y represents an at least partially fluorinated aliphatic or aromatic group, m represents an integer equal to or greater than 1, and n represents an integer such that $0 \leq n \leq 12$.

The invention also relates to the electrically conducting polymers containing recurring units derived from monomers chosen from the substituted thiophenes.

9 Claims, 1 Drawing Sheet

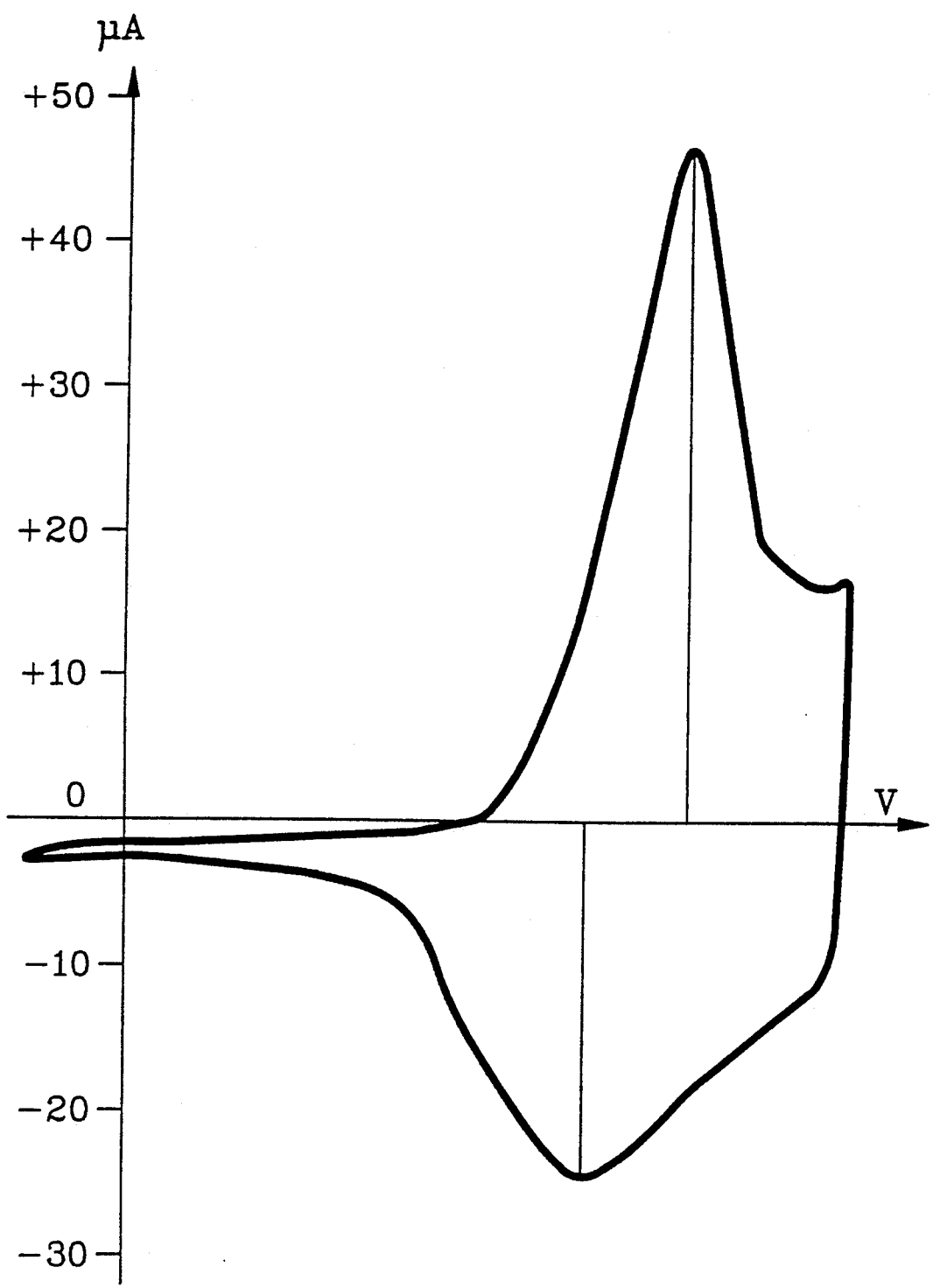

CONDUCTING POLYMERS DERIVED FROM FLUORINATED THIOPHENES

CROSS-REFERENCE TO RELATED APPLICATION

This application is a continuation of application Ser. No. 07/547,071, filed Jul. 3, 1990, now abandoned.

FIELD OF THE INVENTION

The present invention relates to thiophenes substituted by an at least partially fluorinated aliphatic or aromatic radical. The invention also relates to the electrically conducting polymers containing recurring units derived from these substituted thiophenes and to a process for the production of the substituted thiophenes and a process for the production of the polymers and the electrically conducting devices containing these polymers.

TECHNOLOGY REVIEW

Electrically conducting polymers derived from monomers of general formula:

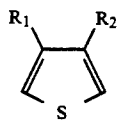

in which $R_1$ may represent, inter alia, an alkyl group substituted by an epoxy, halogenated or carboxylic acid group and $R_2$ represents a hydrogen atom or a methyl radical, have been described in European Patent Application EP 203,438 (Allied Corporation).

However, some electrical applications, such as the production of devices based on electrochromism (display screens, switches, memory elements etc.) involve a modification of the light absorption or transmission properties of the material used, induced by a variation in the external voltage applied; the production of electrodes of rechargeable batteries, photovoltaic cells and electrochemical cells; the production of electromagnetic wave-absorption devices, etc. demand conducting polymers having particular properties.

These particular properties are, especially, the most complete possible electrochemical reversibility, the highest possible stability of the oxidation-reduction cycle between the oxidized and reduced forms of the polymer/doping-agent system, a significant variation in the spectral characteristics obtained with the smallest possible variation in potential, a good electrical conductivity and significant absorptions in the region of the near infrared and high frequency radiations.

SUMMARY OF THE INVENTION

The present invention aims to provide a new family of substituted thiophenes which enable, in particular, electrically conducting polymers to be obtained which have the particular properties mentioned above to a high degree.

BRIEF DESCRIPTION OF THE DRAWING

The FIGURE shows a voltammogram produced with an imposed potential of 1,8 V with a scanning of 20 mV/s in 0.1 mole of lithium perchlorate dissolved in $CH_3CN$; the abscissa unit is the volt (V), the ordinate unit is the microampere ($\mu A$), the minimum ($Ep_c$) is at 0.76 V and the maximum ($EP_a$) is at 0.92 V.

DETAILED DESCRIPTION OF THE INVENTION

To this end, the invention relates to the monomers derived from substituted thiophenes of general formula:

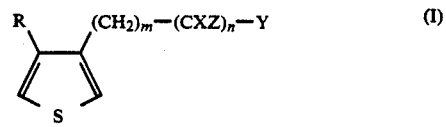

in which:
R represents a hydrogen atom or an aliphatic group containing from 1 to 4 carbon atoms,
X and Z may be identical or different and represent a hydrogen atom or a fluorine atom,
Y represents an at least partially fluorinated aliphatic or aromatic group,
m represents an integer equal to or greater than 1, and
n represents an integer such that $0 \leq n \leq 12$.

Usually:
R represents a hydrogen atom,
X and Z represent a hydrogen atom or a fluorine atom,
Y represents:
  a phenyl radical substituted at least by a fluorine atom or by a —$CF_3$ group, a —$CH_2F$ group or a $CHF_2$ group, or
  an aliphatic group of general formula —$(CF_2)_p$—$CF_3$ in which p represents an integer such that $0 \leq p \leq 16$,
m represents an integer equal to or greater than 1, and
n represents an integer such that $0 \leq n \leq 12$.

Generally:
R represents a hydrogen atom,
X and Z represent a fluorine atom or a hydrogen atom,
Y represents:
  a phenyl radical substituted by a fluorine atom or by a —$CF_3$ group or entirely substituted by fluorine atoms, or
  an aliphatic group of general formula —$(CF_2)_p$—$CF_3$ in which p represents an integer such that $0 \leq p \leq 12$,
m represents an integer such that $1 \leq m \leq 5$, and
n represents an integer such that $0 \leq n \leq 10$.

Preferably:
R represents a hydrogen atom,
X and Z represent a fluorine atom or a hydrogen atom,
Y represents an aliphatic group of general formula $(CF_2)_p$—$CF_3$ in which P represents an integer such that $1 \leq p \leq 8$,
n is 0 or 1.

Particularly preferably:
R represents a hydrogen atom,
X and Z represent a fluorine atom,
Y represents an aliphatic group of general formula —$(CF_2)_p$—$CF_3$ in which p represents an integer equal to 2, 3 or 4,
m is 3, and
n is 1.

The substituted thiophenes according to the invention can be synthesized by diverse methods.

Several methods can be used, as illustrated by schemes (1) and (2) for reaction of the compounds of the following general formulae, in which R, X, Z, Y, m and n are as defined above and m'=(m−1),:

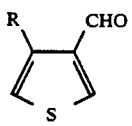

either, with I—(CH₂)ₘ'—(CHZ)ₙ—Y or Br—(CH₂)ₘ'—(CXZ)ₙ—Y in the presence of zinc, magnesium, manganese or cadmium, and preferably in the presence of zinc, and in the presence of pyridine, at 20° C., or in the presence of Y—(CXZ)ₙ—(CH₂)ₘ'—MG—I and diethyl ether

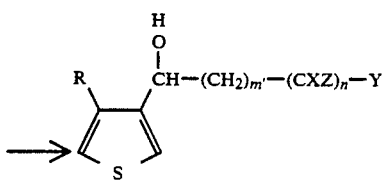

in the presence of SOCl₂, CHCl₃ under reflux

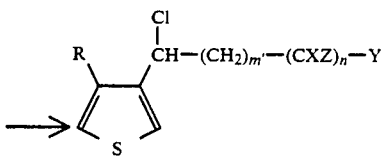

in the presence of LiAlH₄, PdCl₂ and tetrahydrofuran

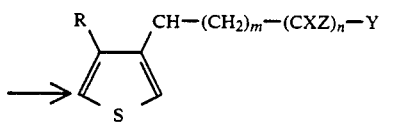 (2)

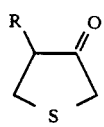

in the presence of Y—(CXZ)ₓ—(CH₂)ₘ—Mg—I and diethyl either

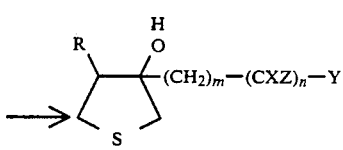

in the presence of tosyl chloride and pyridine

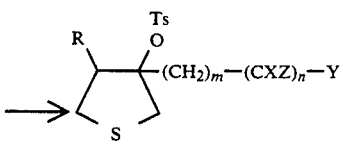

in the presence of KHSO₄ and sulphur at 180° C.

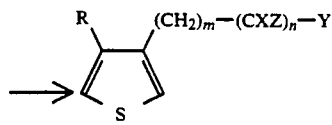

The temperature at which these reactions are carried out is generally between 0° and 200° C.

The pressure at which these reactions are carried out is generally between 1 and 4 bars, and preferably these reactions are carried out under atmospheric pressure.

The reactions are preferably carried out under an inert gas atmosphere, such as, in particular, argon, and in the presence of a solvent, such as, in particular, tetrahydrofuran, and can be carried out in any reactor or apparatus enabling the abovementioned conditions to be combined.

The invention further relates to the polymers containing recurring units derived from substituted thiophene according to the invention.

To this end, the invention relates to polymers of general formula:

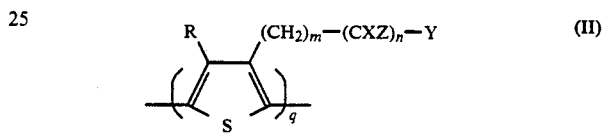 (II)

in which:

q represents an integer,

R represents a hydrogen atom or an aliphatic group containing from 1 to 4 carbon atoms, X and Z may be identical or different and represent a hydrogen atom or a fluorine atom, Y represents an at least partially fluorinated aliphatic or aromatic group, m represents an integer equal to or greater than 1, and n represents an integer such that $0 \leq n \leq 12$.

q represents an integer between 2 and 5000,

R represents a hydrogen atom,

X and Z represent a hydrogen atom or a fluorine atom,

Y represents:

a phenyl radical substituted at least by a fluorine atom or by a —CF₃ group, a —CH₂F group or a CHF₂ group, or an aliphatic group of general formula —(CF₂)ₚ—CF₃ in which p represents an integer such that $0 \leq p \leq 16$, m represents an integer equal to or greater than 1, and n represents an integer such that $0 \leq n \leq 12$.

Generally:

q represents an integer between 2 and 3000,

R represents a hydrogen atom,

X and Z represent a fluorine atom or a hydrogen atom,

Y represents:

a phenyl radical substituted by a fluorine atom or by a —CF₃ group or entirely substituted by fluorine atoms, or an aliphatic group of general formula —(CF₂)ₚ—CF₃ in which p represents an integer such that $0 \leq p \leq 12$, m represents an integer such that $1 \leq m \leq 5$, and Preferably:

q represents an integer between 2 and 1000,

R represents a hydrogen atom,

X and Z represent a fluorine atom or a hydrogen atom,

Y represents an aliphatic group of general formula —$(CF_2)_p$—$CF_3$ in which p represents an integer such that $1 \leq p \leq 8$,
is 2 or 3, and
n represents an integer equal to 0 or 1.
Particularly preferably:
R represents a hydrogen atom,
X and Z represent a fluorine atom,
Y represents an aliphatic group of general formula —$(CF_2)_p$—$CF_3$ in which p represents an integer equal to 2, 3 or 4,
m is 3, and
n is 1.

Good results have been obtained with poly(3-1H,1H,2H,2H,3H,3H-perfluoroheptyl]-thiophene) and poly(3-[1H,1H,2H,2H,3H,3H-perfluorononyl]-thiophene).

The invention also relates to the electrically conducting polymers containing a polymer according to the invention and a doping agent. The doping agent can be an anion or a cation, as defined below.

The preparation of the electrically conducting polymers according to the invention can be carried out by a chemical route, for example in the presence of oxidizing agents, or by an electrochemical route. Good results have been obtained when the procedure used is electrochemical polymerization, generally in an electrolytic cell, by anodic oxidation of the monomer in a polar solvent and in the presence of appropriate electrolytes in accordance with the conventional techniques such as are described, in particular, in French Patent Application FR-A-2,527,843.

According to these techniques, the monomer concentration is generally between $10^{-3}$ and 1 mole per litre of solvent.

The temperature at which the preparation of the polymers is carried out is generally between 0° and 50° C. and preferably between 5° and 40° C.

The pressure at which the preparation of the polymers is carried out is generally close to atmospheric pressure and preferably is equal to atmospheric pressure.

The solvents used are preferably polar solvents which possess dissolving properties both for the monomer and for the electrolyte chosen and are stable in the range of potentials applied. Examples of solvents which can be used are acetonitrile, methylene chloride, nitrobenzene and propylene carbonate.

The electrolytes are generally chosen from the conducting salts of formula $C^+A^-$ in which $C^+$ is a cation and in which $A^-$ is an anion.

The cation $C^+$ is preferably chosen from the alkali metal ions and the ions $R_4N^+$ and $R_4P^+$ (R being an alkyl radical, such as the ethyl and butyl radicals for example).

The anion $A^-$ is preferably chosen from the ions $ClO_4^-$, $AsF_6^-$, $SbF_6^-$, $C_6H_5SO_3^-$, $BF_4^-$, $PF_6^-$ and $CF_3SO_3^-$.

Typical electrolytes are, for example, fluorophosphates, such as tetrabutylammonium hexafluorophosphate, fluoborates, such as tetraethylammonium tetrafluoborate, and perchlorates, such as lithium perchlorate and tetrabutylammonium perchlorate.

The electrolyte concentration is generally between $10^-$ and 1 mole per litre of solvent.

The electrochemical cell in which the polymerization of the monomers according to the invention can be carried out can operate under potentiostatic or galvanostatic conditions.

In the first case (potentiostatic control), the cell comprises, apart from the external current source, three electrodes, one of which is a reference electrode for monitoring the potential.

In the course of the electrolysis, a layer of polymer deposits on the conducting element used as the anode in the electrolytic cell. This anode can be made of a noble metal, such as gold or platinum, or of another metal, such as gold- or platinum-plated copper, titanium, nickel or a conducting glass (tin oxide, indium oxides—tin). After the electrolysis, an electrode is thus in fact available which consists of a conducting body coated with a film of polymer adhering thereto and which contains a certain proportion of the anion originating from the electrolyte. The polymer and the anion thus form a charge transfer complex. The chemical composition of the polymer film can be represented by the empirical formula $(M^+A y^-)_q$ where $M^+$ represents the monomer, $A^-$ the anion or counter-ion, y the proportion of anion in the polymer expressed per monomer unit (that is to say the degree of doping), which, in the case of the polymers of the invention, can reach a value of 0.5, and q the degree of polymerization, which generally is difficult to determine.

As the electrochemical polymerization of the monomer takes place on the anode of the electrolytic cell, it is not possible directly to obtain an electrode covered by a polymer doped by cations.

In order to obtain such an electrode (cathode) it is possible to use the anode obtained above and to subject it to a double reduction. A first electrochemical reduction is possible just after the polymerization by leaving the anode in the electrolytic cell and by bringing about the discharge of the cell. This discharge causes the extraction of the anions "doping" the polymer. A second reduction can then be carried out under an inert atmosphere, either by a chemical route or by an electrochemical route. The chemical route consists in immersing the polymer in a solution containing the desired cations. Thus, in order to obtain a polymer "doped", for example, by the cations $Li^+$, $Na^+$ or $K^+$, it is possible, for example, to make use of a solution of naphthalene-lithium, naphthalene-sodium or naphthalene-potassium in tetrahydrofuran. The electrochemical route generally consists in placing the electrode as the cathode in an electrolytic cell containing the desired cations in solution. The cations can be, for example, alkali metal ions, such as those mentioned above, preferably the $Li^+$ or $K^+$ cations, or complex ions such as $(Bu)_4N^+$ or $(Et)_4N^+$ originating from an electrolyte (preferably $LiClO_4$, $KPF_6$, $(Bu)_4NClO_4$ and $(Et)_4NClO_4$) in solution in a solvent such as acetonitrile or propylene carbonate. The electrolyte concentration in the solution is generally between $10^{-3}$ and 1 mole per 1 litre of solvent.

The conducting polymers according to the invention have an altogether surprising set of properties which are, in the main:
excellent reversibility and stability of the oxidationreduction cycle between their oxidized and reduced forms;
a significant variation in the spectral characteristics obtained with a small variation in potential, which makes their use as electrochromic material worthwhile and economical;

a good electrical conductivity, generally of between 1 and $2 \times 10^2$ S.cm$^{-1}$;

significant absorptions in the region of the near infrared and high frequency radiations.

The conducting polymers according to the invention have a good thermal and chemical stability and have hydrophobicity and biocompatibility properties. Poly(3-1H,1H,2H,2H,3H,3H-perfluoroheptyl]-thiophene) has an elasticity of more than 30%.

These surprising properties of the conducting polymers according to the invention make them suitable for use, in particular, for the production of electrically conducting devices for which the principle of operation is based on these properties and which are also a subject of the present invention.

The following may be mentioned as non-limiting examples of electrically conducting devices containing conducting polymers derived from the substituted aromatic heterocyclic monomers according to the invention:

electrochemical devices for storing energy, such as batteries of accumulators and batteries which may or may not be rechargeable, in which the anodes (or the cathodes) consist of electrodes coated with films of the said polymers doped by anions (or, respectively, cations);

electrochromic devices based on the modification of the optical spectrum of the said polymers depending on their oxidation state, which manifests itself during the oxidation and reduction cycles of films of polymers deposited on the anodes (or the cathodes) of these devices during charging and discharging; examples of devices which may be mentioned are display screens, optoelectronic devices and optical memories and switches;

electromagnetic wave-absorption devices.

The invention is illustrated by the following examples.

EXAMPLE 1

Synthesis of 3-(1H,1H,2H,2H,3H,3H-perfluorononyl)-thiophene a) Synthesis of the alcohol

A solution of 2.9 g (25.8 mmols) of (3-thienyl)-methanal in 20 cc of diethyl ether is introduced into a three-necked 100 cm$^3$ flask fitted with a condenser surmounted by a calcium chloride trap, an argon inlet, a dropping funnel and a thermometer.

A solution of 1H,1H,2H,2H-perfluorooctylmagnesium iodide, which has previously been prepared by mixing 0.65 g (0.027 atom.g$^{-1}$) of magnesium, 11.9 g (0.025 atom.g.:) of 1H,1H,2H,2H-perfluorooctyl iodide and 20 cc of diethyl ether, is then introduced into the dropping funnel.

The flask is then cooled to 5° C. and the solution of the magnesium compound is introduced dropwise into the flask.

The reaction mixture thus obtained is stirred at ambient temperature for 12 hours and is then hydrolysed with 20 ml of a 2N solution of hydrochloric acid.

The organic phase is extracted with 4 times 10 ml of a 38% solution of NaHSO$_3$, then with twice 20 ml of water. The organic phase is then dried over magnesium sulphate and evaporated under vacuum. A yellow oil is obtained which is purified on silica using heptane/ethyl acetate, 7/3 (by volume), as the eluent.

10.0 g of a colourless oil, which crystallizes, are recovered.

Finally, 5.94 g of pure alcohol [thienyl-(1H,1H,2H,2H-perfluorooctyl)methanol] are obtained with a yield of 52%.

b) Synthesis of the chlorinated compound 4.5 g (0.01 mol) of this alcohol (molecular weight=459.25), 5 cc of chloroform and 2 ml (27 mmols) of thionyl chloride are mixed.

This reaction mixture is kept under reflux for one hour.

It is then evaporated under vacuum and the residue is taken up in twice 10 ml of methanol and the solution is again evaporated under vacuum. The residue is then taken up in 20 ml of chloroform.

The solution is then washed with a saturated solution of sodium bicarbonate until neutral.

A colourless oil is obtained with a yield of 95% [1-chloro-3-(1H,2H,2H,3H,3H-perfluorononyl)-thiophene] (molecular weight=478.7).

c) Synthesis of the fluorinated thiophene 4.5 g (9.5 mmols) of the chlorinated compound obtained, 2 g (11.3 mmols) of anhydrous PdCl$_2$ and 10 ml of anhydrous tetrahydrofuran are introduced into a three-necked 100 cm$^3$ flask fitted with a condenser surmounted by a calcium chloride trap, an argon inlet and a device for the introduction of powders (sock).

0.4 g (10.5 mmols) of lithium aluminium hydride are then introduced slowly after having purged with argon.

The reaction mixture is stirred for 2 hours at ambient temperature. It is then poured slowly onto crushed ice and left to stand for 12 hours at 20° C.

The palladium is then decanted and the organic phase is extracted with diethyl ether. The extract is dried over magnesium sulphate.

It is then evaporated under vacuum.

A colourless oil is obtained.

It is purified on a silica column using pentane as the eluent.

The solvent is evaporated.

3.7 g of a colourless oil which crystallizes at $-4°$ C. are obtained; the yield is 80%.

3—(1H,1H,2H,2H,3H,3H-Perfluorononyl)-thiophene is obtained in a total yield of 50%.

EXAMPLE 2

The synthesis of the polymer is carried out in a thermostat-controlled single-compartment 50 cm$^3$ electrochemical cell containing:

$1 \times 10^{-1}$ mole of monomer prepared as in Example 1, $-2 \times 10^{-2}$ moles of tetrabutylammonium hexafluorophosphate (provided by Fluka), 25 ml of distilled nitrobenzene.

The polymer deposits are produced at 20° C., under an argon atmosphere, after degassing the solution by bubbling argon through it. For the electrochemical characteristics, the polymer is deposited on a polished solid platinum electrode having a surface area of 0.07 cm$^2$. The amount of charges used is 100 mC/cm$^2$ and the current density is 2 mA/cm$^2$. The cathode consists of a platinum wire and the reference electrode is a saturated calomel electrode.

The electrical conductivity of the polymer thus obtained is of the order of 12 S.cm$^{-1}$.

The electrochemical properties of the polymers were measured from the cyclic voltammogram recorded using a PAR model 173 potentiostat and from the intensity peaks recorded. The figure shows a voltammogram produced with an imposed potential of 1.8 V with a scanning rate of 20 mV/s in 0.1 mole of lithium perchlorate dissolved in $CH_3CN$; the abscissa unit is the volt (V), the ordinate unit is the microampere ($\mu A$), the minimum ($Ep_c$) is at 0.76 V and the maximum ($EP_a$) at 0.92 V.

The $Ip_a/Ip_c$ ratios between the current intensities for oxidation ($Ip_a$) and reduction ($Ip_c$) (for the system p) are about 1.2.

The doping "p" of the polymer is highly reversible. The charge exchanged after 5000 cycles between $-0.2$ and 1.25 volt at 200 mV/s is still 90%, the polymer being doped and dedoped by 10% each time, or 50% of the maximum charge exchanged under slow cycling (20 mV/s).

We claim:

1. A thiophene of general formula:

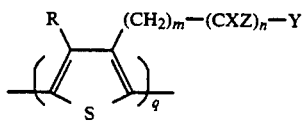 (II)

in which
q represents an integer between 2 and 500,
R represents a hydrogen atom,
X and Z each represent a fluorine atom,
Y represents an aliphatic group of formula—$(CF_2)_p$—$CF_3$ in which p represents an integer equal to 2, 3 or 4, or an at least partially fluorinated aromatic group,
m is 3, and
n is 1.

2. The thiophene set forth in claim 1, wherein Y represents an aliphatic group and p is 2.

3. The thiophene set forth in claim 1, wherein Y represents an aliphatic group and p is 3.

4. The thiophene set forth in claim 1, wherein Y represents an aliphatic group and p is 4.

5. The thiophene set forth in claim 1, having an electrical conductivity about 12 $S.cm^{-1}$.

6. The thiophene set forth in claim 1, having an electrical conductivity between about 1 and $2 \times 10^{-2}$ $S.cm^{-1}$.

7. A thiophene as set forth in claim 1, namely poly(3-[1H,1H,2H, 2H, 3H,3H-perfluoroheptyl]-thiophene).

8. A thiophene as set forth in claim 1, namely poly(3-[1H,1H,2H, 2H, 3H,3H-perfluoroheptyl]-thiophene).

9. A thiophene as set forth in claim 1, wherein:
q represents an integer between 2 and 500,
R represents a hydrogen atom,
X and Z represent a fluorine atom,
Y represents an at least partially fluorinated aromatic group,
m is 3, and
n is 1.

* * * * *